United States Patent [19]

Grand

[11] 4,312,855
[45] Jan. 26, 1982

[54] COMPOSITIONS CONTAINING AMINOPOLYUREYLENE RESIN

[75] Inventor: Paul S. Grand, South Bound Brook, N.J.

[73] Assignee: Colgate-Palmolive Company, New York, N.Y.

[21] Appl. No.: 760,619

[22] Filed: Jan. 14, 1977

Related U.S. Application Data

[60] Continuation of Ser. No. 308,883, Nov. 22, 1972, abandoned, which is a division of Ser. No. 90,154, Nov. 16, 1970, Pat. No. 3,726,815.

[51] Int. Cl.$^3$ .......................... A61K 7/06; A61K 7/42; A61K 31/74
[52] U.S. Cl. ...................................... 424/59; 252/106; 252/107; 424/60; 424/70; 424/78; 424/329
[58] Field of Search ............................. 424/59, 60, 78

[56] References Cited

U.S. PATENT DOCUMENTS 3,726,815 4/1973 Grand .................................. 252/544

Primary Examiner—Dale R. Ore
Attorney, Agent, or Firm—Richard N. Miller; Murray M. Grill; Herbert S. Sylvester

[57] ABSTRACT

Compositions comprising a mixture of an aminopolyureylene resin having a molecular weight in the range of about 300 to 100,000 and an active material selected from the group of antibacterial materials, tarnish inhibitors, ultra violet absorbers, fluorescent brighteners, bluing agents and skin treating materials, the weight ratio of resin to active material being effective to improve the properties of the active material and being selected from the range of 1:1 to 20:1. Preferred compositions comprise 2% to 99% by weight of a water-soluble organic detergent, 0.05% to 5% by weight of aminopolyureylene resin and 0.05 to 5% by weight of active material.

18 Claims, No Drawings

COMPOSITIONS CONTAINING AMINOPOLYUREYLENE RESIN

This is a continuation, of application Ser. No. 308,883 filed Nov. 22, 1972, now abandoned which is a division of application Ser. No. 90,154, filed Nov. 16, 1970, now U.S. Pat. No. 3,726,815.

The invention relates to improved compositions comprising a water-soluble and/or water-insoluble active material having the capacity to impart a residual characteristic to surfaces treated therewith such as antibacterial compounds, tarnish inhibitors, ultra-violet absorbers, fluorescent brighteners, bluing agents and skin treating materials and an aminopolyureylene (APU) resin in an amount effective to enhance the effects of the active materials. The APU resins appear to enhance the deposition and/or retention of the water-soluble and water-insoluble active substances on the surfaces contacted therewith.

The capacity of the APU resin to improve the effectiveness of the active materials on surfaces contacted therewith surprisingly is maintained in the presence of water-soluble organic detergents and, therefore, detergent compositions containing the mixture of active material and APU resin represent preferred embodiments. Such detergent compositions include dishwashing detergents, shampoos, laundry detergents, hard-surface cleaners and toilet bars. The effectiveness of the APU resins in the presence of minor and major amounts of water-soluble organic detergents is surprising because the effectiveness of the active materials is due to the deposition and/or retention of the active materials on surfaces contacted therewith and detergents normally tend to minimize deposition and retention of such materials on the washed surfaces. Thus, usually only a small percentage of the active materials in a detergent composition is actually retained on a particular surface or substrate after washing and, optionally, rinsing. Accordingly, to achieve a particular level of activity, the concentration of active material must be increased-with an attendant increase in cost—when used as a component in a detergent composition.

While the mechanism by which the improved effects are obtained is not understood, it appears that the APU resin may unite either with the active material or the contacted surface to increase the affinity of the active material for the surface. In many cases, an increase in the weight of active material retained by the surface has been quantitatively verified. However, no absolute mechanism has been defined and the invention is not limited to any particular theory.

Generally, the improved compositions of this invention consist essentially of a mixture of an aminopolyureylene resin having a molecular weight in the range of about 300 to 100,000 and a water-soluble or water-insoluble active material having the capacity to impart a residual property to surfaces treated therewith and selected from the group consisting of (A) antibacterial compounds, (B) tarnish inhibitors, (C) ultra-violet absorbers, (D) optical brighteners, (E) bluing agents and (F) skin-treating compounds, the weight ratio of resin to active material being effective to improve the effects of the active material and selected from the range of 1:1 to 20:1 preferably 1:1 to 5:1. Preferred compositions are detergent compositions comprising 2% to 99% by weight of a water-soluble, organic detergent, 0.05% to 5% by weight of aminopolyureylene resin and about 0.05 to 5% by weight of active material.

Also, within the scope of the invention is a method for improving the effectiveness of active materials on surfaces contacted therewith which comprises contacting the surface with a water solution or dispersion of the active material and an effective amount of the aminopolyureylene resin sufficient to improve the effect of the active material retained on the treated surface after the contacting solution is removed.

The APU resins suitable for use in the described compositions and method have a molecular weight in the range of about 300 to 100,000 and are characterized by the following repeating unit:

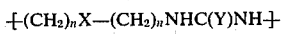

wherein X is NH, N-$C_1$ to $C_{22}$ alkyl,

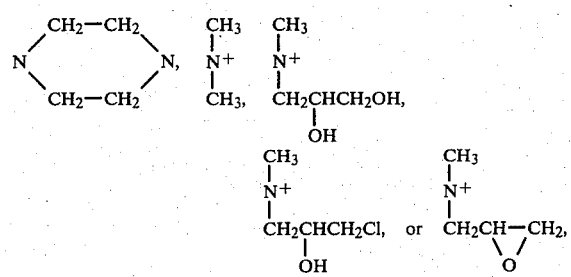

Y is O or S, and n is 2 or 3.

Such APU resins and their cosmetic effectiveness are set forth in the copending application of Paul Grand entitled "Cosmetic Compositions" filed of even date herewith.

Thus, suitable APU resins include both the polyurea- and the polythiourea-containing compounds. Preferred APU resins have a repeating unit where Y is oxygen, n is 3, and X is selected from the group consisting of N—$C_{18}$ alkyl and

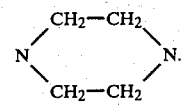

Generally, the number of repeating units in the resin will be sufficient to yield a polymer having a molecular weight in the range of about 300 to 100,000. Preferred APU resins have an average molecular weight in the range of 1,000 to 20,000 and a particularly preferred resin is the reaction product of equimolar quantities of N-methyl, bis(3-amino-propyl) amine and urea having a molecular weight of about 4,300.

The molecular weight of the APU resins is based upon aqueous gel permeation chromatographic analysis. The separation is carried out in oxalic acid solution, adjusted to pH 3.5, on three Corning controlled-pore glass columns (nominal pore sizes 175,125 and 75 Å) in series. Detection is by differential refractometer. Reference compounds are dextran polysaccharides of molecular weights of 150,000, 110,000, 40,000, 20,000 and 10,000 and sucrose and galactose.

The APU resins which can be used in the compositions of this invention are prepared by reacting, for example, 145 grams of N-methyl bis(3-aminopropyl) amine (1.0 mole) and 60 grams of urea (1.0 mole) in a 3-necked flask equipped with a therometer, mechanical stirrer, condenser, and nitrogen sparge tube. Nitrogen is bubbled slowly through the solution throughout the course of the reaction. The solution is heated to 140° C. over a 20-minute interval where ammonia begins to evolve. The solution is further heated to 250° C. over a 30-minute interval and allowed to cool. The product is a hard, resinous powder (Resin A) having a molecular weight of about 4,300. The secondary amine analogues can be made by the above process if bis(3-aminopropyl) amine or bis(2-aminoethyl) amine are reacted with urea or thiourea. The piperazine analogues are made by reacting N,N'-di(3-aminopropyl)piperazine or N,N'-di(2-aminoethyl)piperazine with urea or thiourea. The N—$C_1$ to $C_{22}$ alkyl analogues are prepared by reacting N—$C_1$ to $C_{22}$ alkyl bis(3-aminopropyl) amine or N—$C_1$ to $C_{22}$ alkyl bis(2-aminoalkyl) amine with urea or thiourea. Additional analogues are prepared by the following reactions:

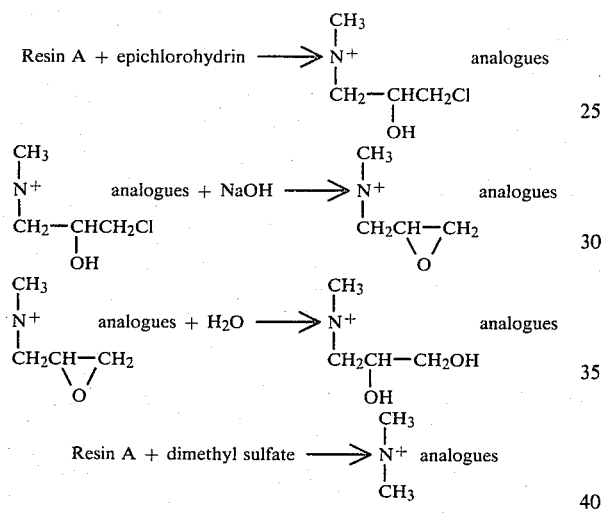

The preparation of the remaining analogues is well within the skill of the art following the above techniques.

The active materials which are potentiated by the APU resin are well known and have been used for treating surfaces and substrates to impart certain residual characteristics to the contacted surfaces. The treated surfaces or substrates include proteinaceous materials such as hair and skin, textiles such as cotton, rayon and synthetic fibers, and porcelain, wood, plastic and metal. Such active materials may be water-soluble such as cetyl dimethyl benzyl ammonium bromide and gelatin or water-insoluble such as zinc 2-pyridinethiol-1-oxide and optical brighteners. To facilitate activity and utility, the water-insoluble materials are usually in the form of finely divided particles having a diameter in the range of about 0.5 to 50 microns. Suitable active materials include antibacterial compounds, tarnish inhibitors, ultra-violet absorbers, optical brighteners, bluing agents and skin treating materials such as hydrolyzed proteins, silicones and polyacrylamides.

Antibacterial compounds which may be used in the compositions include water-soluble and water-insoluble salts of 2-pyridinethiol-1-oxide, substituted salicylanilides, substituted carbanilides, halogenated bisphenols, mono-higher alkyl quaternary ammonium salts, and 5,7 diiodo-8-hydroxyquinoline.

Preferred antibacterial compounds include the water-insoluble salts, e.g., zinc, cadmium, zirconium, tin and aluminum, and water-soluble salts, e.g., sodium and potassium, of 2-pyridinethiol-1-oxide which has the following structural formula in tautomeric form.

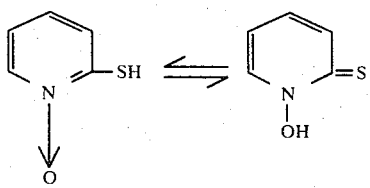

The zinc and sodium salts of 2-pyridinethiol-1-oxide are particularly preferred.

Other suitable antibacterial compounds are the substituted bisphenols having the formula

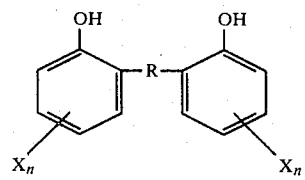

wherein X is a halogen such as chlorine or bromine, n is 1–3 and R is an alkylene of 1–4 carbon atoms or divalent sulfur. Typical compounds include bis(3,5,6-trichloro-2-hydroxyphenyl) methane or sulfide, bis(5-chloro-2-hydroxyphenyl)methane and bis(3,5-dichloro-2-hydroxyphenyl)methane or sulfide.

Suitable antibacterial substituted salicylanilides have the structural formula

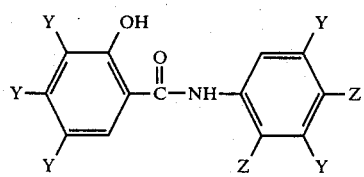

wherein Y is hydrogen, halogen, or trifluoromethyl and Z is hydrogen or halogen. Among the suitable salicylanilides are 3,4',5'-tribromosalicylanilide; 5—bromosalicyl—3,5—di(trifluoromethyl)anlide; 5—chlorosalicycl—3,5—di(trifluoromethyl)anlide; 3,5—dichlorosalicyl—3,4—dichloroanilide; and 5—chlorosalicyl—3—trifluoromethyl—4—chloroanilide. These and other useful salicylanilides are disclosed in U.S. Patent No. 2,703,332.

Satisfactory substituted carbanilides have the following general structure

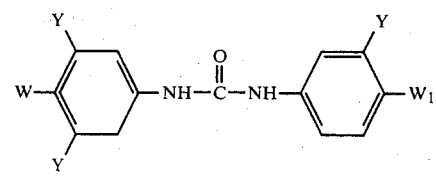

wherein Y is hydrogen, halogen, or trifluoromethyl, W is halogen or ethoxy, and $W_1$ is hydrogen or halogen. Included among the suitable carbanilides are 3,4,4'-trichlorocarbanilide; 4,4'-trifluoromethyl-3'4,4'-trichlorocarbanilide; 3,3'-bis(trifluoromethyl—4—ethoxy—4'—chlorocarbanilide; and 3,5—bis(trifluoromethyl)—4'—chlorocarbanilide.

Other antibacterial materials are the mono-higher-alkyl quaternary ammonium salts having the following structural formula:

$$\left[\begin{array}{c} R_2 \\ | \\ R_1-N-R_3 \\ | \\ R_4 \end{array}\right]^+ A^-$$

wherein $R_1$ is $C_8$ to $C_{22}$ alkyl, $R_2$ and $R_3$ are each $C_1$–$C_3$ alkyl, $R_4$ is $C_1$–$C_3$ alkyl or benzyl and A is an anion selected from the group consisting of chlorine, bromine, iodine, and methosulfate. A preferred compound is cetyl trimethyl ammonium bromide.

Additional useful antimicrobial compounds include 5,7-diiodo-8-hydroxy quinoline, 1,6-di(4'chlorophenyl-diquanado)hexane, and 5-chloro-2(2,4-dichlorophenoxy)phenol, $C_8$ to $C_{22}$ isoquinolinium halides, such as lauryl isoquinolinium bromide, and $C_8$–$C_{22}$ alkyl pyridinium halide.

The tarnish inhibitors potentiated by APU resins include, for example, benzotriazole and ethylenethiourea.

Ultraviolet absorbers potentiated by APU resins have the structural formula

[Structure: benzophenone with Z, OH, Y, X substituents]

where X, Y, and Z are selected from the group consisting of hydrogen, hydroxy, $C_1$ to $C_8$ alkoxy and carboxy, at least one of said X, Y, and Z being oxy. Preferred compounds include 2-hydroxy-4-n-octoxy-benzophenone and 2-hydroxy-4-methoxy-2'-carboxy-benzophenone.

The optical or fluoroescent brightener active materials which are potentiated by the APU resins are selected from the group consisting of stilbene disulfonates, quaternized aminoalkyl substituted phenyl sulfonamides of aryl pyrazolines, substituted styrylnaphth oxazoles, and substituted aminocoumarins.

Suitable stilbene disulfonate fluorescent brighteners have the formula formula

[Structure with triazines linked by stilbene-SO₃Na groups]

wherein X is OH,

[Structure: NH-phenyl-N(morpholine)-N(CH₂CH₂OH)₂]

or NH—[phenyl]—OCH₃ and Y is NH—[phenyl],

N(CH₂CH₂OH)₂, or NH—[phenyl]—OCH₃.

Suitable compounds are disodium 4,4' bis [4-anilino-6-methoxyanilino-s-triazin-2yl amino]-2,2' stilbene disulfonate and disodium 4,4' bis(4,6 dianilino-s-triazin-2yl amino) 2,2' stilbene-disulfonate.

Suitable quaternized aminoalkyl substituted phenyl sulfonamides of aryl pyrazoline have the following formula:

$$\begin{array}{c} Y \\ | \\ N \\ X-HC \diagdown N \\ | \quad | \\ H_2C \text{———} CH-X \end{array}$$

Wherein X is hydrogen, phenyl, or halogenated phenyl with not more than one X being hydrogen and Y is a quaternized

[phenyl]—SO₂NHRN(R₁)(R₂)

wherein R is $C_1$–$C_4$ alkyl and $R_1$ and $R_2$ are each elected from the group consisting of hydrogen and $C_1$–$C_3$ alkyl. A typical compound is quaternized-1-p(sulfonyl-γ-dimethyl aminopropyl amido)-phenyl-3-p-chlorophenyl pyrazoline.

Suitable oxazole fluorescent brighteners have the structural formula:

[Structure: naphth-oxazole with C—CH=CH—phenyl substituent, R groups]

wherein A and B are different and represent oxygen and nitrogen, and R represents individually hydrogen, alkyl groups having 1 to 6 carbon atoms, chlorine or fluorine. A preferred oxazole brightener is 2-styrlnaphth (1,2-d) oxazole.

Additional fluorescent brighteners potentiated by APU resin are the water-soluble substituted aminocoumarins having the following structural formula:

[Structure: aminocoumarin with R groups]

wherein R is hydrogen or $C_1$-$C_2$ alkyl. A preferred compound is 4 methyl, 7 dimethyl amino coumarin.

A bluing material which is potentiated by APU resin is ultramarine blue. This is a well-known blue pigment occurring naturally as mineral the lapis lazuli. It can be made, for example, by igniting a mixture of kaolin, sodium carbonate or sulfate, sulfur, and carbon. It is insoluble in water and is stable when in contact with bleaching agents, alkali, and light. Details for synthetic ultramarines are given in the text "Ultramarines, Their History and Characteristic," Reckitts (Colours) Ltd., Hull, England. Preferred are micropulverized, synthetic ultramarine blues, particularly grades RS4–RS8 provided by Reckitts. The pigment is in the form of particles substantially all of which exhibit a diameter of less than about 0.05 millimeter, and is characterized by the ability to impart a faint blue visible shade to fabrics treated therewith without staining such fabrics when used at recommended concentration and fashion, being generally considered to be non-substantive, or at least non-accumulative, on fabrics.

The skin-treating materials which are enhanced by the APU resins are the water-soluble, substantive proteins. Such proteins are substantive to the hair and skin in the presence of detergents. Suitable proteins are water-soluble polypeptides, having a molecular weight in the range of about 120 (amino acid) to about 20,000, preferably from about 800 to 12,000. Such polypeptides are obtained by hydrolysis of protein materials such as hides, gelatin, collagen, and the like, with collagen protein being preferred, using well-known processes. During hydrolysis the protein materials are gradually broken down into their constituent polypeptides and amino acids by prolonged heating with acids, e.g., sulfuric acid, or alkalis, e.g., sodium hydroxide, or treatment with enzymes, e.g., peptidases. First, high molecular weight polypeptides are formed, and as hydrolysis proceeds these are converted progressively to simpler and simpler polypeptides, to tripeptides, dipeptides, and finally to amino acids. It is obvious that the polypeptides derived from proteins are complex mixtures. The preferred hydrolysates are obtained from bone- or skin-derived collagen protein by enzymatic hydrolysis and are sold under the trade names "WSP-X-250" and "WSP-X-1000" of Wilson Pharmaceutical and Chemical Corporation.

Other skin-treating materials whose skin-slip or antifriction properties are enhanced by APU resins include ethylene oxide polymers having a molecular weight in the range of about 500,000 to 1,000,000 which are sold under the trade name "Polyox."

The water-soluble organic detergent materials which can be used in forming the preferred detergent compositions of this invention may be selected from the group consisting of anionic, nonionic, amphoteric, zwitterionic, polar nonionic, and cationic detergents, and mixtures of two or more of the foregoing detergents.

The anionic surface-active agents include those surface-active or detergent compounds which contain an organic hydrophobic group containing generally 8 to 26 carbon atoms and preferably 10 to 18 carbon atoms in their molecular structure, and at least one water-solubilizing group selected from the group of sulfonate, sulfate, carboxylate, phosphonate and phosphate so as to form a water-soluble detergent.

Examples of suitable anionic detergents which fall within the scope of the anionic detergent class include the water-soluble salts, for example, the sodium, ammonium, and alkylolammonium salts, of higher fatty acids or resin salts containing about 8 to 20 carbon atoms, preferably 10 to 18 carbon atoms. Suitable fatty acids can be obtained from oils and waxes of animal or vegetable origin, for example, tallow, grease, coconut oil, tall oil and mixtures thereof. Particularly useful are the sodium and potassium salts of the fatty acid mixtures derived from coconut oil and tallow, for example, sodium coconut soap and potassium tallow soap.

The anionic class of detergents also include the water-soluble sulfated and sulfonated synthetic detergents having an alkyl radical of 8 to 26, and preferably about 12 to 22 carbon atoms. (The term alkyl includes the alkyl portion of the higher acyl radicals.)

Examples of the sulfonated anionic detergents are the higher alkyl mononuclear aromatic sulfonates such as the higher alkyl benzene sulfonates containing from 10 to 16 carbon atoms in the higher alkyl group in a straight or branched chain, for example, the sodium, potassium, and ammonium salts of higher alkyl benzene sulfonates, higher alkyl toluene sulfonates, higher alkyl phenol sulfonates and higher naphthalene sulfonates. A preferred sulfonate is linear alkyl benzene sulfonate having a high content of 3- (or higher) phenyl isomers and a correspondingly low content (well below 50%) of 2- (or lower) phenyl isomers, that is, wherein the benzene ring is preferably attached in large part at the 3 or higher (for example, 4, 5, 6 or 7) position of the alkyl group and the content of the isomers in which the benzene ring is attached in the 2 or 1 position is correspondingly low. Particularly preferred materials are set forth in U.S. Pat. No. 3,320,174.

Other suitable anionic detergents are the olefin sulfonates, including long-chain alkene sulfonates, long-chain hydroxyalkane sulfonates or mixtures of alkene sulfonates and hydroxyalkane sulfonates. These olefin sulfonate detergents may be prepared in a known manner by the reaction of $SO_3$ with long-chain olefins containing 8 to 25, preferably 12 to 21 carbon atoms and having the formula $RCH=CHR_1$ where R is a higher alkyl group of 6 to 23 carbons and $R_1$ is an alkyl group or 1 to 17 carbons or hydrogen to form a mixture of sultones and alkene sulfonic acids which is then treated to convert the sultones to sulfonates. Other examples of sulfate or sulfonate detergents are paraffin sulfonates containing about 10 to 20 and preferably about 15 to 20 carbon atoms, for example, the primary paraffin sulfonates are made by reacting long-chain alpha olefins and bisulfites and paraffin sulfonates having the sulfonated group distributed along the paraffin chain as shown in U.S. Pat. Nos. 2,503,280; 2,507,088; 3,260,741; 3,372,188; and German Pat. No. 735,096; sodium and potassium sulfates of higher alcohols containing 8 to 18 carbon atoms such as sodium lauryl sulfate and sodium tallow alcohol sulfate; sodium and potassium salts of α-sulfofatty acid esters containing about 10 to 20 carbon atoms in the acyl group, for example, methyl α-sulfomyristate and methyl α-sulfotallowate, ammonium sulfates of mono- or di-glycerides of higher ($C_{10}$-$C_{18}$) fatty acids, for example, stearic monoglyceride monosulfate; sodium and alkylolammonium salts of alkyl polyethenoxy ether sulfates produced by condensing 1 to 5 moles of ethylene oxide with one mole of higher ($C_8$-$C_{18}$) alcohol; sodium higher alkyl ($C_{10}$-$C_{18}$) glyceryl ether sulfonates; and sodium or potassium alkyl phenol polyethenoxy ether sulfates with about 1 to 6 oxyethylene groups per molecule and in which the alkyl radicals contain about 8 to about 12 carbon atoms.

The suitable anionic detergents include also the $C_8$ to $C_{18}$ acyl sarcosinates (for example, sodium lauryl sarcosinate), sodium and potassium salts of the reaction product of higher fatty acids containing 8 to 18 carbon atoms in the molecule esterified with isethionic acid, and sodium and potassium salts of the $C_8$ to $C_{18}$ acyl N-methyl taurides, for example, sodium cocoyl methyl taurate and potassium stearoyl methyl taurate.

Anionic phosphate surfactants in which the anionic solubilizing group attached to the hydrophobic group is an oxyacid of phosphorous are also useful in the detergent compositions. Suitable phosphate surfactants are the sodium, potassium, and ammonium alkyl phosphate esters such as $(R-O)_2PO_2M$ and $ROPO_3M_2$ in which R represents an alkyl chain containing from about 8 to 20 carbon atoms or an alkyl phenyl group having 8 to 20 carbon atoms and M represents a soluble cation. The compound formed by including about 1 to 40 moles of ethylene oxide in the foregoing esters, for example, $[R-O(EtO)n]_2PO_2M$, are also satisfactory.

The particular anionic detergent salt will be suitably selected, depending upon the particular formulation and the proportions therein. Suitable salts include the ammonium, substituted ammonium (mono-, di-, and triethanolammonium), alkali metal (such as sodium and potassium) and alkaline earth metal (such as calcium and magnesium) salts. Preferred salts are the ammonium, triethanolammonium, sodium, and potassium salts of the higher alkyl sulfates and the $C_8$ to $C_{18}$ acyl sarcosinates.

The nonionic synthetic organic detergents are generally the condensation product of an organic aliphatic or alkyl aromatic hydrophobic compound and hydrophilic ethylene oxide groups. Practically any hydrophobic compound having a carboxy, hydroxy, amido, or amino group with a free hydrogen attached to the nitrogen can be condensed with ethylene oxide or with the polyhydration product thereof, polyethylene glycol, to form a nonionic detergent. Further, the length of the polyethenoxy chain can be adjusted to achieve the desired balance between the hydrophobic and hydrophilic elements.

The nonionic detergents include the polyethylene oxide condensate of one mole of alkyl phenol containing from about 6 to 12 carbon atoms in a straight- or branched-chain configuration with about 5 to 30 moles of ethylene oxide, for example, nonyl phenol condensed with 9 moles of ethylene oxide, dodecyl phenol condensed with 15 moles of ethylene and dinonyl phenol condensed with 15 moles of ethylene oxide. Condensation products of the corresponding alkyl thiophenols with 5 to 30 moles of ethylene oxide are also suitable.

Still other suitable nonionics are the polyoxyethylene polyoxypropylene adducts of 1-butanol. The hydrophobe of these anionics has a minimum molecular weight of 1,000 and consists of an aliphatic monohydric alcohol containing from 1 to 8 carbon atoms to which is attached a heteric chain of oxyethylene and oxypropylene. The weight ratio of oxypropylene to oxyethylene covers the range of 95:5 to 85:15. Attached to this is the hydrophilic polyoxyethylene chain which is from 44.4 to 54.6 of the total molecular weight.

Also included in the nonionic detergent class are the condensation products of a higher alcohol containing about 8 to 18 carbon atoms in a straight or branched-chain configuration condensed with about 5 to 30 moles of ethylene oxide. for example, lauryl-myristyl alcohol condensed with about 16 moles of ethylene oxide.

A particularly useful group of nonionics is marketed under the trade name "Pluronics." The compounds are formed by condensing ethylene oxide with a hydrophobic base formed by the condensation of propylene oxide with propylene glycol. The molecular weight of the hydrophobic portion of the molecule is of the order of 950 to 4,000 and preferably 1200 to 2500. The addition of polyoxyethylene radicals to the hydrophobic portion tends to increase the solubility of the molecule as a whole. The molecular weight of the block polymers varies from 1,000 to 15,000, and the polyethylene oxide content may comprise 20% to 80% by weight.

Zwitterionic detergents such as the betaines and sulfobetaines having the following formula are also useful:

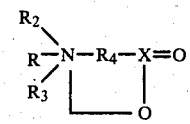

wherein R is an alkyl group containing about 8 to 18 carbon atoms, $R_2$ and $R_3$ are each an alkylene or hydroxyalkylene group containing about 1 to 4 carbon atoms, $R_4$ is an alkylene or hydroxyalkylene group containing 1 to 4 carbon atoms, and X is C or S:O. The alkyl group can contain one or more intermediate linkages such as amido, ether, or polyether linkages or nonfunctional substituents such as hydroxyl or halogen which do not substantially affect the hydrophobic character of the group. When X is C, the detergent is called a betaine; and when X is S:O, the detergent is called a sulfobetaine or sultaine. Preferred betaine and sulfobetaine detergents are 1-(lauryl dimethylammonio) acetate, 1-(myristyl dimethylammonio) propane-3-sulfonate, and 1-(myristyldimethylammonio)-2-hydroxy-propane-3-sulfonate.

The polar nonionic detergents are those in which the hydrophilic group contains a semi-polar bond directly between two atoms, for example, N→O, P→O, As→O, and S→O. There is charge separation between the two directly bonded atoms, but the detergent molecule bears no net charge and does not dissociate into ions.

The polar nonionic detergents of this invention include open-chain aliphatic amine oxides of the general formula $R_1R_2R_3N\rightarrow O$. For the purpose of this invention $R_1$ is an alkyl, alkenyl, or monohydroxyalkyl radical having about 10 to 16 carbon atoms, $R_2$ and $R_3$ are each selected from the group consisting of methyl, ethyl, propyl, ethanol, and propanol radicals.

Other operable polar nonionic detergents are the open-chain aliphatic phosphine oxides having the general formula $R_1R_2R_3P\rightarrow O$ wherein $R_1$ is an alkyl, alkenyl, or monohydroxyalkyl radical ranging in chain length from 10 to 18 carbon atoms, and $R_2$ and $R_3$ are each alkyl and monohydroxyalkyl radicals containing from 1 to 3 carbon atoms.

Examples of suitable ampholytic detergents include the alkyl beta-aminopropionates, $RN(H)C_2H_4COOM$; the alkyl betaiminodipropionates, $RN(C_2H_4COOM)_2$; the alkyl and hydroxy alkyl taurinates, $RN(CH_3)C_2H_4SO_3M$; and the long-chain imidazole derivatives having the following formulas:

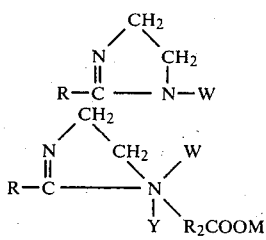

wherein R is an acylic group of about 7 to 17 carbon atoms, W is selected from the group of $R_2OH$, $R_2COOM$, and $R_2OR_2COOM$, Y is selected from the group consisting of $OH^-$, $R_3OSO_3^-$, $R_2$ is an alkylene or hydroxyalkylene group containing 1 to 4 carbon atoms, $R_3$ is selected from the group consisting of alkyl, alkyl aryl and fatty acyl glyceride groups having 6 to 18 carbon atoms in the alkyl or an acyl group; and M is a water-soluble cation, for example, sodium, potassium, ammonium, for alkylolammonium.

Formula I detergents are disclosed in Volume II of "Surface Active Agents and Detergents" and Formula II detergents are described in U.S. pat. Nos. 2,773,068; 2,781,354; and 2,781,357. The acyclic groups may be derived from coconut oil fatty acids (a mixture of fatty acids containing 8 to 18 carbon atoms), lauric fatty acid, and oleic fatty acid, and the preferred groups are $C_7$ to $C_{17}$ alkyl groups. Preferred detergents are sodium N-lauryl beta-aminopropionate, disodium N-lauryl iminodipropionate, and the disodium salt of 2-lauryl-cycloimidium-1-hydroxyl, 1-ethoxyethanoic acid, 1-ethanoic acid.

Cationic surface active agents may also be employed. Such agents are those surface active detergent compounds which contain an organic hydrophobic group and a cationic solubilizing group. Typical cationic solubilizing groups are amine and quaternary groups.

Examples of suitable synthetic cationic detergents are normal primary amines $RNH_2$ wherein R is $C_{12}$ to $C_{15}$; the diamines such as those of the type $RNHC_2H_4NH_2$ wherein R is an alkyl group of about 12 to 22 carbon atoms, such as N-2-aminoethyl stearyl amine and N-2-aminoethyl myristyl amine; amide-linked amines such as those of the type $R_1CONHC_2H_4NH_2$ wherein $R_1$ is an alkyl group of 8 to 20 carbon atoms, such as N-2-amino ethylstearyl amide and N-amino ethylmyristyl amide; quaternary ammonium compounds wherein typically one of the groups linked to the nitrogen atom is an alkyl group of about 8 to 22 carbon atoms and three of the groups linked to the nitrogen atom are alkyl groups which contain 1 to 3 carbon atoms, including alkyl groups bearing inert substituents, such as phenyl groups, and there is present an anion such as halogen, acetate, methosulfate, etc. The alkyl group may contain intermediate linkages such as amide which do not substantially affect the hydrophobic character of the group, for example, stearyl amide propyl quaternary ammonium chloride. Typical quaternary ammonium detergents are ethyl-dimethyl-stearyl ammonium chloride, benzyl-dimethylstearyl ammonium chloride, trimethyl-stearyl ammonium chloride, trimethyl-cetyl ammonium bromide, dimethyl-ethyl-lauryl ammonium chloride, dimethyl-propyl-myristyl ammonium chloride, and the corresponding methosulfates and acetates.

Preferred detergent compositions of this invention are the liquid, antimicrobial shampoo compositions suitable for washing the hair and scalp. Such compositions consist essentially of about 10% to 40% by weight of a detergent selected from the group consisting of non-soap anionic, amphoteric, and zwitterionic detergents from 0.1% to 3% by weight of water-soluble or water-insoluble particulate antimicrobial active material, 0.5% to 3.5% of aminopolyureylene resin, and the balance primarily water. The shampoo compositions may also include minor amounts of ethanol or isopropanol, perfume, color, stearate opacifying agents, ethylene diamine tetracetate or citrate sequestering agents, thickening agents, and fatty acid alkylolamide foam boosters.

Other detergent compositions falling within the scope of the invention are the heavy-duty laundering compositions containing APU polymers and at least one of the active materials potentiated by the polaminopolyureylene resins, such as antibacterials, fluorescent brighteners, and bluing agents. Such compositions generally consist essentially of about 8% to 40% by weight of non-soap anionic or nonionic detergent, about 0.1% to 3% by weight of active material, about 0.5% to 3.5% by weight of APU resin and the balance water-soluble inorganic or organic builder salt. Suitable builders include sodium sulfate, sodium carbonate, and sodium nitrilotriacetate as well as the corresponding potassium compounds. Other compositions are sodium carboxymethylcellulose, polyvinylalcohol, perfume, color, etc.

The foregoing laundering detergents may also be prepared in liquid form. Suitable liquids consist essentially of about 5% to 20% by weight of non-soap anionic or nonionic detergent, 10% to 25% by weight of potassium pyrophosphate, sodium silicate or sodium nitrilotriacetate, 4% to 12% by weight of sodium or potassium xylene or toluenesulfonate, 0.1% to 3.0% by weight of active material, 0.5% to 3.5% by weight of APU resin, and the balance primarily water. Suitable additives which may be added are sodium carboxymethylcellulose, thickeners, color, and perfume.

In bar form, the detergent material may be soap, anionic, amphoteric, nonionic or mixtures of the foregoing detergents. In addition to the usual proportions of APU resin and active material, the bars may include color, perfume, free fatty acids, sodium chloride, and fatty acid alkanolamide suds builders.

Each of the foregoing detergent compositions can be prepared by methods well known in the art. For example, shampoos and built liquid detergents are prepared by mixing, and particulate laundering detergents are prepared by mixing, chemical drying or spray drying.

The ability of the APU resins to potentiate the deposition of the water-insoluble materials which function as antibacterial agents onto proteinaceous substrates, such as hair and skin, is demonstrated in the following radioactive substantivity test. Substantivity is determined by stirring a 1.27-centimeter diameter circular gelatin disk weighing about 40 milligrams for about five minutes in 10 grams of an aqueous medium containing a known concentration of radioactive tagged material such as zinc 2-pyridinethiol-1-oxide, rinsing the disk five times in 10 milliliters of water, drying, and measuring the radiation emission with the aid of a radiation detector. The absolute degree of deposition of the material is determined by comparing the observed counts with the counts emitted by a known weight of the radioactive material. The effect of APU resin on deposition can be readily ascertained by repeating the test with a known weight of APU present. Similarly, the effect of detergents can be quantitatively measured by including detergents in the test composition.

The following examples are illustrative of the compositions falling within the scope of this invention.

EXAMPLE 1

An aqueous dispersion of zinc 2-pyridinethiol-1-oxide is prepared by dispersing 0.04 grams of radioactive zinc 2-pyridinethiol-1-oxide containing zinc 65 in one gram of water. The resultant aqueous dispersion is diluted with 8.96 grams of water with agitation, and the substantivity of the diluted dispersion is determined using the foregoing substantivity procedure. The results of the evaluation indicate 40.9 micrograms of zinc-2-pyridinethiol-1-oxide are deposited on the disk from the aqueous mixture containing 0.4% by weight of the 2-pyridinethiol-1-oxide. When the foregoing experiment is repeated in the presence of an amino polyureylene resin (Resin A) having a molecular weight of about 4,300 and the repeating unit $+(CH_2)_3N(CH_3(CH_2)_3N(H)C(O)N(H)+$, 122 micrograms of zinc 2-pyridinethiol-1-oxide are deposited on the disk at a concentration of 0.5% of said resin in the aqueous test dispersion. Thus, the presence of 0.5% of APU resin results in a 200% increase in the deposition of zinc-2-pyridinethiol-1-oxide from an aqueous medium.

Use of a resin having a molecular weight of about 5,600 and N,N'-di(3-aminopropyl) piperazine as the repeating unit in the foregoing test yields comparable results.

EXAMPLE 2

When the procedure of Example 1 is repeated using an aqueous solution of 0.25% by weight of radioactive (C-14) cetyl trimethylammonium bromide (CTAB) at pH 4.5 as the test medium, 294 micrograms of CTAB are deposited on the gelatin disk. Repetition of this test in the presence of 0.75% by weight of the APU resin used in Example 1 results in the deposition of 679 micrograms of CTAB, an increase in deposition of about 130%. When the pH of the test solution is increased to 8.5, a deposition of 259 micrograms of CTAB is obtained in the absence of APU resin and a deposition of 734 micrograms is obtained in the presence of 3% by weight of the APU resin of Example 1. Thus, a 180% increase in deposition of CTAB is noted at pH 8.5.

EXAMPLE 3

Example 2 is repeated with the exception that a 10% aqueous ethanol mixture is substituted for water in the test solution and the pH is adjusted to 6.5. A deposition value of 202 micrograms of CTAB is noted in the absence of APU resin, and a deposition value of 643 micrograms of CTAB is noted in the presence of 0.75% by weight of the APU resin of Example 1. This represents an increase in deposition of about 220%. For comparison, only 227 micrograms of CTAB are deposited when the concentration of CTAB in the test solution is increased to 1% by weight. Thus, the APU resin is significantly more effective in enhancing deposition than an increase in the CTAB concentration from 0.25% to 1%, a 300% increase.

EXAMPLE 4

When the procedure of Example 1 is repeated using a 0.5% by-weight aqueous alcoholic (70%) dispersion of radioactive (C-14) bis(3,5,6 -trichloro-2-hydroxyphenyl) methane as the test solution, the radioactivity of the gelatin disk averages 2,100 counts per minute (cpm.) Repetition of the test in the presence of 1.25% concentration of the APU resin of Example 1 results in an average radioactivity of 13,200 cpm. Thus, the presence of the APU resin increases the deposition of the antimicrobial compound by about 500%. Substantially similar results are noted when either lamb skin or human callus tissue is substituted for the gelatin disk in the foregoing experiment.

The APU resin of Example 1 can be replaced by either a resin having a molecular weight of about 4,600 and the repeating unit $+(CH_2)_3N^+(CH_3)_2(CH_2)_3NH-C(O)NH+$ or a resin having a molecular weight of about 6,700 and the repeating unit

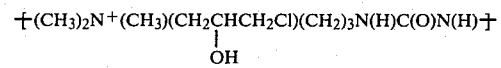

with substantially similar results. Similarly, the substituted methane may be substituted with 5-chloro-2(2,4 dichlorophenoxy) phenol with substantially similar results.

EXAMPLE 5

Tests of the following shampoo illustrate the improved effects attributable to the APU resin. This shampoo is effective to inhibit the growth of *Pityrosporum ovale*.

|  | % by weight |
| --- | --- |
| Triethanolamine lauryl sulfate | 10 |
| Lauryldimethyl amine oxide | 10 |
| Cocomonoethanol amide | 5 |
| Ethyl alcohol | 10 |
| Zinc 2-pyridinethiol-1-oxide | 1.6 |
| Resin A[a] | 2.0 |
| Water | Balance |
|  | 100.0 |

[a]Aminopolyureylene resin having a molecular weight of about 4,300 and a repeating unit of $+(CH_2)_3N(CH_3)(CH_2)_3N(H)C(O)N(H)+$ When the foregoing composition is formulated with a radioactive zinc 2-pyridinethiol-1-oxide (Zn 65) material and is evaluated using the substantivity procedures of Example 1, 20.8 micrograms of radioactive zinc 2-pyridinethiol-1-oxide are noted on the gelatin disk. In this evaluation, 2.5 grams of shampoo are diluted with 7.5 grams of water to simulate normal use dilution of shampoos, and the diluted shampoo is test solution. Under such conditions, the concentration of zinc 2-pyridinethiol-1-oxide in the test solution is 0.4% by weight, and the concentration of APU resin is 0.5% by weight. Repetition of the foregoing test with an identical composition not containing APU resin results in the deposition of 8.7 micrograms of zinc 2-pyridinethiol-1-oxide. Thus, use of APU resin in combination with zinc 2-pyridinethiol-1-oxide in the presence of detergents results in an increase in deposition of about 140%.

To confirm that increased deposition results in enhanced residual activity, radioactive disks obtained using the foregoing evaluation technique are plated in a standard agar medium inoculated with *P. ovale*, and the diameters of the zone of inhibition are measured after twenty-four hours of incubation. These results are shown in Table I together with results of nonradioactive disks. Resin A alone has no zone of inhibition.

TABLE I

| Zinc 2-pyridinethiol-1-oxide | APU resin | Zone of inhibition after 24 hours (m.m.) |
|---|---|---|
| Radioactive | No | 24.9 |
| Radioactive | Yes | 40.3 |
| Non-radioactive | No | 20.1 |
| Non-radioactive | Yes | 43.5 |

The foregoing results indicate that APU resin significantly improves the antibacterial effectiveness of the zinc 2-pyridinethiol-1-oxide. Further, the results show that radioactivity has a minimal effect on the results.

The effect of APU resin on long-standing activity is illustrated by repeatedly transferring the radioactivity disks of Table I to freshly seeded agar plates inoculated with *P. ovale* for additional incubation periods after measuring the zone of inhibition. Results are set forth in Table II.

TABLE II

| APU Resin | Zone of inhibition (m.m.) | | |
|---|---|---|---|
| | One Incubation | Two Incubations | Three Incubations |
| No | 24.9 | 5.8 | 0 |
| Yes | 43.5 | 24.5 | 9.4 |

These results indicate that the presence of APU resin results in improved antimicrobial effectiveness of the zinc-2-pyridinethiol-1-oxide and longer-lasting effectiveness.

EXAMPLE 6

Example 5 is repeated with the exception that the concentration of zinc 2-pyridinethiol-1-oxide in the shampoo is reduced to 0.4%. 17.4 micrograms of zinc 2-pyridinethiol-1-oxide are deposited on the disk. In the absence of the 2% of APU resin, 6.1 micrograms of zinc 2-pyridinethiol-1-oxide are deposited on the disk. Again, APU resin significantly enhances the deposit of zinc 2-pyridinethiol-1-oxide on a proteinaceous substrate.

EXAMPLE 7

The following liquid detergent composition is an effective antimicrobial detergent.

| | % by weight |
|---|---|
| Sodium lauryl triethenoxy ether sulfate | 8.0 |
| Lauryl dimethyl amine oxide | 7.5 |
| Sodium 2-pyridinethiol-1-oxide | 2.0 |
| Resin A | 1.0 |
| Water | Balance |
| | 100.0 |

When the composition is formulated with radioactive sodium 2-pyridinethiol-1-oxide, the zone of inhibition determined as described in Example 5, the gelatin disk exhibits a halo diameter of 54.2 m.m. when tested against *P. ovale*. In the absence of APU resin, a halo diameter of 37.5 m.m. is observed. These results show that APU resin improves the effectiveness of the water-soluble sodium 2-pyridinethiol-1-oxide material as well as the water-insoluble zinc-2-pyridinethiol-1 oxide.

EXAMPLE 8

Another antimicrobial liquid detergent composition having a pH of 8.2 follows.

| | % by weight |
|---|---|
| Cocoamidopropyl dimethyl betaine* | 22.4 |
| Sodium N-(2 hydroxyhexadecyl) methyl taurate | 6.0 |
| Sodium hexylbenzene sulfonate | 0.8 |
| Lauryl dimethyl amine oxide | 0.6 |
| Tribromosalicylanilide | 1.0 |
| Resin A | 3.0 |
| Water | Balance |
| | 100.0 |

*Coco corresponds to the mixture of alkyls derived from a middle cut of coconut oil, that is, 1% $C_{10}$, 65% $C_{12}$, 27% $C_{14}$, and 7% $C_{16}$.

When the foregoing composition is formulated with a radioactive (C-14 tagged) tribromosalicylanilide and the deposition evaluated as described in Example 1, 1.5 micrograms of antibacterial agent are noted on the gelatin disk. As only 0.5 micrograms are deposited in the absence of the APU resin, use of the APU resin increases deposit by 200%.

EXAMPLE 9

Substitution of 1% of trichlorocarbanilide for the tribromosalicylanilide in the composition of Example 8 yields substantially similar results.

EXAMPLE 10

A lotion shampoo composition exhibiting effectiveness against *P. ovale* follows.

| | % by weight |
|---|---|
| Triethanolamine lauryl sulfate | 12.5 |
| Triethanolamine dodecylbenzene sulfonate | 7.8 |
| Diethanolamine soap (19 oleic: 1 coco fatty acid) | 3.0 |
| Lauric-myristic diethanolamide | 4.0 |
| Glycerin | 5.0 |
| Sorbitol | 3.5 |
| Diethanolamine | 1.9 |
| Monosodium phosphate | 0.5 |
| Sodium chloride | 0.2 |
| Formaldehyde | 0.1 |
| Resin A | 3.0 |
| 5, 7-diiodo-8 hydroxyquinoline | 3.0 |
| Water | Balance |
| | 100.0 |

When the foregoing shampoo having a pH of 8.8 is formulated with radioactive 5,7-diiodo-8-hydroxyquinoline (I-125) and the deposition evaluated using the procedure of Example 5, the APU resin results in a 220% increase in the deposition of the antimicrobial agent. Improved deposition is also obtained when the pH of the composition to 7.8.

When the concentration of 5,7-diiodo-8-hydroxyquinoline is reduced to 1% in the composition of Example 10, APU resin achieves a 133% increase in deposition of that agent.

EXAMPLE 11

The following composition is an improved shampoo composition.

| | % by weight |
|---|---|
| Triethanolamine lauryl sulfate | 21 |

| | % by weight |
|---|---|
| Coconut monoethanolamide | 5 |
| Triethanolamine | 0.7 |
| Sodium chloride | 0.8 |
| Methyl cellulose | 0.9 |
| Ethanol | 7.0 |
| Resin A | 3.0 |
| Fluorescent agent | 1.0 |
| Water | Balance |
| | 100.0 |

When the foregoing composition is formulated with the fluorescent agents listed in Table III and a 1.25% concentration thereof is used to contact a 1″×1″ wool swatch for five minutes, the fluorescent values in Table III are obtained on the wool swatch after it is rinsed with five consecutive 10-milliliter portions of water and air dried.

TABLE III

| Fluorescent Agent | Resin | Relative Fluorescence |
|---|---|---|
| Disodium 4,4′bis[4-anilino-6-methoxyanilino-5-triazin-2yl-amino]-2,2′-stilbene disulfonate | No | 11 |
| | Yes | 12 |
| Quaternized 1-p-(sulfonyl-γ-dimethyl-aminopropyl amido)-phenyl-3-p-chlorophenyl-pyrazoline | No | 27 |
| | Yes | 74 |
| 2-strylnaphth (1,2-d) oxazole | No | 15 |
| | Yes | 30 |
| Disodium 4,4′bis[4,6-dianilino-s-triazin-2yl-amino]-2,2′-stilbene disulfonate | No | 47 |
| | Yes | 55 |
| Substituted amino-coumarin purchased under the trade name "Uvitex SWN" | No | 87 |
| | Yes | 93 |

The foregoing results show that APU resins improve the brightening effectiveness of fluorescent agents of the anionic type (stilbene disulfonate), nonionic (oxazole) and the cationic type (pyrazoline). The improvement noted in fluorescence varies from 7% to 200%.

EXAMPLE 12

The following composition is an improved conditioning shampoo.

| | % by weight |
|---|---|
| $C_{10}$ to $C_{16}$ alkyl* amidopropyl dimethyl betaine | 16.0 |
| Triethanolamine lauryl sulfate | 4.0 |
| Lauryl dimethyl amine oxide | 0.5 |
| Polyoxypropylene-polyoxyethylene block copolymer having a hydrophobic molecular weight of 1,750 and containing 20% by weight of polyoxyethylene | 5.0 |
| Condensation product of 1:1 mixture of ethylene oxide and propylene oxide on butanol (mol. wt. 4,000) | 2.0 |
| Resin A | q.s. |
| Ethanol | 1.9 |
| Protein** | q.s. |
| Water, perfume | balance |
| | 100.0 |

*Alkyl group corresponds to the mixture of alkyls obtained from middle cut of coconut oil
**Wilson Protein WSP-X250 obtained by enzymatic hydrolysis of collagen and having an average molecular weight of about 1,000

The effectiveness of the aminopolyureylene resin in improving the conditioning properties of the protein is shown by the following procedure. A bleached hair tress about 2.5 inches (weight 0.55 grams) is placed in contact with 55 grams of the shampoo composition of Example 12 and the contact is maintained for 30 minutes. The hair tress is then removed from the shampoo, subjected to five consecutive rinses with 55 milliliters of deionized water each time, air dried, and analyzed spectrophotometrically for hydroxyproline. (Hydroxyproline is an amino acid found in hydrolyzed protein, but not in hair). The protein and aminopolyureylene resin are soluble in the shampoo composition having a pH of 7.5 and the test results for the composition are set forth in Table IV.

TABLE IV

| Protein % by weight | Resin A % by weight | Protein Deposited (1) % by weight |
|---|---|---|
| 2.2 | 0 | 0.08 |
| 0.55 | 0 | 0.08 |
| 2.2 | 0.4 | 0.125 |
| 0.55 | 1.0 | 0.10 |
| 0.55 | 3.0 | 0.08 |
| 0.055 | 1.0 | 0.09 |

(1) Hydroxyproline content expressed as protein.

The foregoing tabulation shows that aminopolyureylene resin improves the deposition of water-soluble protein onto hair and thereby achieves improved conditioning effects.

Substitution of a benzophenone ultraviolet absorber or a silicone for the gelatin in Example 12 provides compositions having substantially similar improved effects.

When resins having an average molecular weight in the range of 1,000 to 20,000 and a repeating unit of

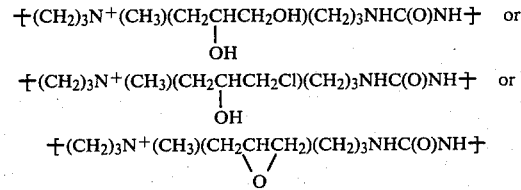

are substituted for the resin in the composition of Example 12, substantially similar results are obtained.

Other compositions exhibiting improved effectiveness because of the presence of an aminopolyureylene resin therein follow:

EXAMPLE 13

A heavy-duty liquid detergent composition having improved resistance to color fading because of ultraviolet light follows:

| | % by weight |
|---|---|
| Sodium tridecylbenzene sulfonate | 10.0 |
| Potassium xylene sulfonate | 8.5 |
| Lauric-myristic diethanolamide | 4.5 |
| Potassium pyrophosphate | 15.0 |
| Sodium carboxymethylcellulose | 0.5 |
| 2,4-dihydroxybenzophenone | 0.05 |
| Hydrogenated castor oil | 0.5 |
| Resin A | 0.5 |
| Water | balance |
| | 100.0 |

2,2′hydroxy4,4′dimethoxybenzophenone may be substituted for the benzophenone in the composition of Example 13 with substantially similar improved effects.

EXAMPLE 14

A built particulate laundry detergent composition exhibiting improved antibacterial effectiveness has the following composition:

| | % by weight |
|---|---|
| Sodium tridecylbenzene sulfonate | 17.5 |
| Sodium tripolyphosphate | 40.0 |
| Sodium silicate (1Na₂O:2.35SiO₂) | 7.0 |
| Sodium sulfate | 23.1 |
| Tribromosalicylanilide | 0.4 |
| Resin A | 3.0 |
| Sodium carboxymethylcellulose | 0.5 |
| Water | 0.5 |
| | 100.0 |

Fabrics laundered in the foregoing composition exhibit improved antimicrobial effectiveness.

EXAMPLE 15

A detergent bar composition exhibiting improved resistance to copper discoloration has the following composition.

| | % by weight |
|---|---|
| Sodium N lauryl B iminodipropionate | 8.75 |
| Sodium C₁₀ to C₂₀ alkane sulfonate | 24.25 |
| Sodium tallow soap | 26.40 |
| Sodium tridecylbenzene sulfonate | 7.30 |
| Syrupy phosphoric acid (85%) | 7.30 |
| Stearic Acid | 3.60 |
| Benzotriazole | 0.5 |
| Resin A | 4.0 |
| Water | balance |
| | 100.00 |

Ethylene thiourea may be substituted for benzotriazole in the composition of Example 15 with substantially similar results.

While the improved properties appear to be due primarily to enhanced deposition and/or retention of both water-soluble and water-insoluble materials due to the presence of the aminopolyureylene resin in the compositions, the actual mechanism is not completely understood. Accordingly, applicant does not wish to be bound by any particular scientific theory or explanation.

While compositions containing APU resin and an active material may be prepared by admixing resin and active material in any suitable manner, in the preparation of detergent containing compositions, improved effects are obtained when the resin and active material are premixed before admixing with the detergent component.

Although the present invention has been described with reference to particular embodiments and examples, it will be apparent to those skilled in the art that similar results may be obtained when the aminopolyureylene resin is used in combination with a wide variety of water-soluble and water-insoluble substances in addition to those specifically described.

What is claimed is:

1. A composition comprising a mixture of an aminopolyureylene resin having a molecular weight in the range of 300 to 100,000 and having the following repeating unit:

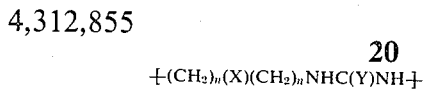

wherein X is NH, N-C₁ to C₂₂ alkyl,

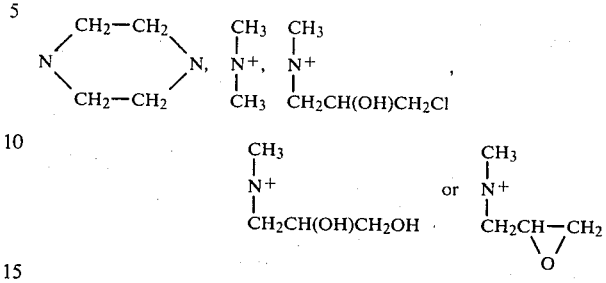

Y is O or S and n is 2 or 3; and an active material selected from the group consisting of (I) antimicrobials, (II) tarnish inhibitors, (III) ultra violet absorbers, (IV) fluorescent brighteners, (V) bluing agents and (VI) skin treating compounds, the weight ratio of resin to active material being effective to improve the properties of the active material and being selected from the range of 1:1 to 20:1.

2. A composition in accordance with claim 1 wherein said active material is selected from the group consisting of: (I) antimicrobial agents selected from the group consisting of (A) water-soluble and water-insoluble salts of 2-pyridinethiol-1-oxide; (B) substituted bisphenols having the formula

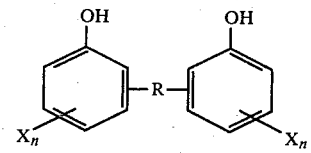

wherein X is halogen, n is 1-3 and R is an alkylene of 1 to 4 carbon atoms or divalent sulfur; (C) substituted salicylanilides having the formula

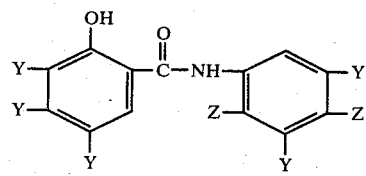

wherein Y is hydrogen, halogen or trifluoromethyl and Z is hydrogen or halogen; (D) substituted carbanilides having the following structure

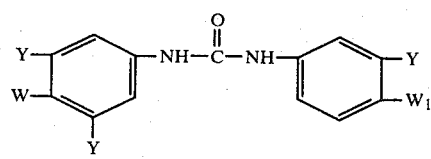

wherein Y is hydrogen, halogen or trifluoromethyl, W is halogen or ethoxy and W₁ is hydrogen or halogen; (E) mono-higher alkyl quaternary ammonium salts selected from the group consisting of C₈ to C₂₂ alkyl isoquinolinium halides, C₈ to C₂₂ alkyl pyridinium halides and salts having the formula

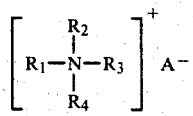

wherein R is $C_8$ to $C_{22}$ alkyl, $R_2$ and $R_3$ are each $C_1$ to $C_3$ alkyl, $R_4$ is $C_1$ to $C_3$ alkyl or benzyl and A is selected from the group consisting of chlorine, bromine, iodine and methosulfate; (F) 5,7-diiodo-8 hydroxyquinoline; (G) 1,6-di-(4'-chlorophenyldiguanado) hexane and (H) 5-chloro-2(2,4-dichlorophenoxy) phenol; (II) tarnish inhibitors selected from the group consisting of benzotriazole and ethylene-thiourea; (III) ultraviolet absorbers having the formula

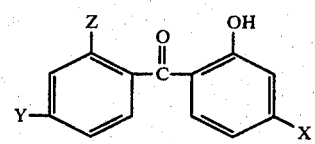

wherein X, Y and Z are each selected from the group consisting of hydrogen, hydroxy, $C_1$ to $C_8$ alkoxy and carboxy, at least one of said X, Y and Z being oxy; (IV) fluorescent brighteners selected from the group consisting of (A) stilbene disulfonates having the formula

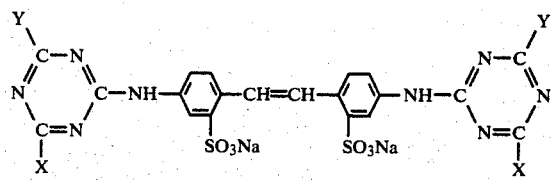

wherein X is OH,

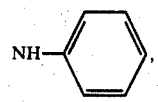

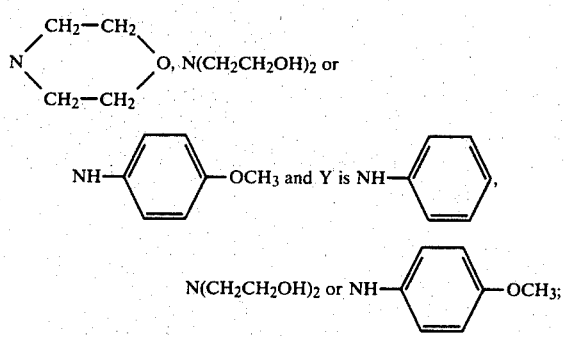

(B) quaternized aminoalkyl substituted phenyl sulfonamide of aryl pyrazolines having the formula

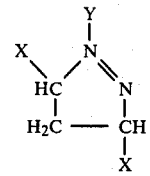

wherein X is hydrogen; phenyl or halogenated phenyl, with not more than one X being hydrogen, and Y is a quaternized

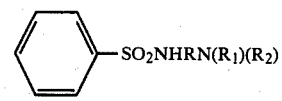

wherein R is $C_1$ to $C_4$ alkyl and $R_1$ and $R_2$ are each selected from the group consisting of hydrogen and $C_1$ to $C_3$ alkyl; (C) oxazoles having the formula

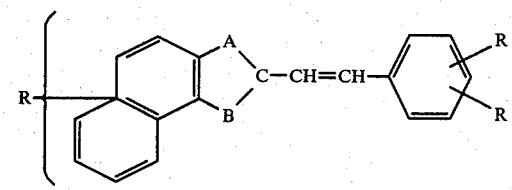

wherein A and B are different and represent oxygen and nitrogen, and R represents individually hydrogen, alkyl groups having 1 to 6 carbon atoms, chlorine or fluorine; and (D) aminocoumarins having the formula

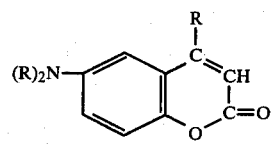

wherein R is hydrogen or $C_1$ to $C_2$ alkyl; (V) ultramarine bluing agents; and (VI) skin treating materials selected from the group consisting of water-soluble polypeptides having a molecular weight of 120 to 20,000 which are derived by hydrolyzing a bone- or skin-derived collagen protein and polyethylene oxides having a molecular weight in the range of 500,000 to 1,000,000.

3. A composition suitable for use in formulating an antimicrobial composition or a hair and skin treating composition consisting essentially of a mixture of aminopolyureylene resin having a molecular weight in the range of 300 to 100,000 and having the following repeating unit:

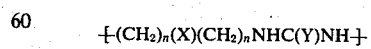

wherein X is NH,N-$C_1$ to $C_{22}$ alkyl,

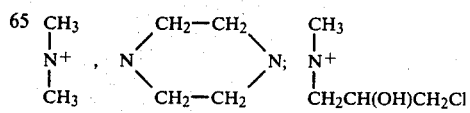

-continued

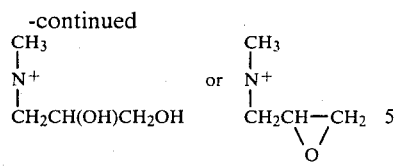

Y is O or S and n is 2 or 3; and an active material selected from the group consisting of (I) an antimicrobial agent selected from the group consisting of (A) water-soluble and water-insoluble salts of 2-pyridinethiol-1-oxide; (B) substituted bisphenols having the formula

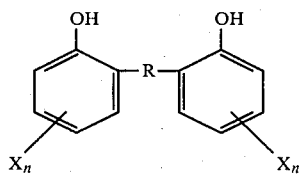

wherein X is halogen, n is 1 to 3 and R is an alkylene of 1 to 4 carbon atoms or divalent sulfur; (C) substituted salicylanilides having the formula

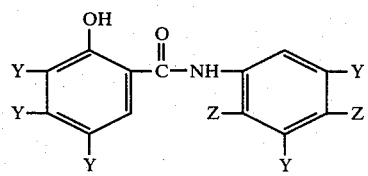

wherein Y is hydrogen, halogen or trifluoromethyl and Z is hydrogen or halogen; (D) substituted carbanilides having the following structure

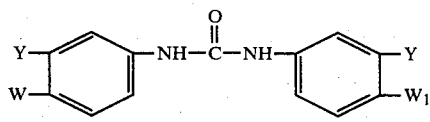

wherein Y is hydrogen, halogen or trifluoromethyl, W is halogen or ethoxy and $W_1$ is hydrogen or halogen; (E) mono-higher alkyl quaternary ammonium salts selected from the group consisting of $C_8$ to $C_{22}$ alkyl isoquinolinium halides, $C_8$ to $C_{22}$ alkyl pyridinium halides and salts having the formula

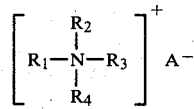

wherein $R_1$ is $C_8$ to $C_{22}$ alkyl, $R_2$ and $R_3$ are each $C_1$ to $C_3$ alkyl, $R_4$ is $C_1$ to $C_3$ alkyl or benzyl and A is selected from the group consisting of chlorine, bromine, iodine and methosulfate; (F) 5,7-diiodo-8-hydroxyquinoline; (G) 1,6-di(4'-chlorophenyldiguanado) hexane and (H) 5-chloro-2(2,4-dichlorophenoxy) phenol; and (II) a skin treating material selected from the group consisting of water-soluble polypeptides having a molecular weight of 120 to 20,000 which are derived by hydrolyzing a bone- or skin-derived collagen protein in the presence of acid, alkali or enzyme and polyethylene oxides having a molecular weight in the range of 500,000 to 1,000,000; the weight ratio of resin to active material being effective to improve the properties of the active material and being selected from the range of 1:1 to 20:1.

4. A composition in accordance with claim 2 wherein said resin has an average molecular weight in the range of 1000 to 20,000 and in said repeating unit Y is O and n is 3.

5. A composition in accordance with claim 4 wherein said active material is zinc pyridinethiol-1-oxide.

6. A composition in accordance with claim 4 wherein said active material is sodium pyridinethiol-1-oxide.

7. A composition in accordance with claim 4 wherein said active material is bis(3,5,6-trichloro-2-hydroxyphenyl)methane.

8. A composition in accordance with claim 4 wherein said active material is cetyl trimethyl ammonium bromide.

9. A composition in accordance with claim 4 wherein said active material is selected from the group consisting of disodium 4,4' bis[4-anilino-6-methoxyanilino-s-triazin-2yl-amine]-2,2' stilbene disulfonate, disodium 4,4' bis(4,6 dianilino-s-triazin-2yl-amino) 2,2' stilbene disulfonate, quaternized-1-p(sulfonyl-γ-dimethyl aminopropyl amido)-phenyl-3-p-chlorophenyl pyrazoline, 2-strylnaphth (1,2-d) oxazole, and 4methyl, 7 diethyl amino coumarin.

10. A composition in accordance with claim 3 wherein said active material is said antimicrobial agent.

11. A composition in accordance with claim 3 wherein said active material is said skin-treating material.

12. A composition in accordance with claim 11 wherein said skin-treating material is said water-soluble polypeptide.

13. A composition in accordance with claim 11 wherein said skin treating material is said polyethylene oxide.

14. A method of improving the deposition and/or retention of an active material on a surface treated with said active material comprising contacting said surface in the presence of water with a mixture of an active material selected from the group consisting of (I) an antimicrobial agent selected from the group consisting of (A) water-soluble and water-insoluble salt of 2-pyridinethiol-1-oxide; (B) substituted bisphenols having the formula

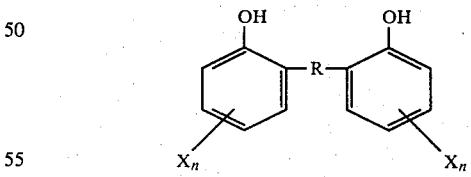

wherein X is halogen, n is 1 to 3 and R is an alkylene of 1 to 4 carbon atoms or divalent sulfur; (c) substituted salicylanilides having the formula

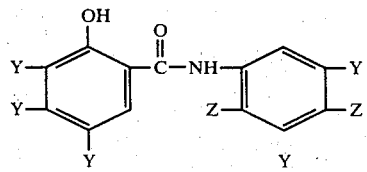

wherein Y is hydrogen, halogen or trifluoromethyl and Z is hydrogen or halogen; (D) substituted carbanilides having the following structure

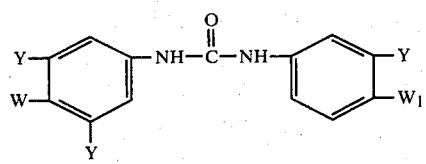

wherein y is hydrogen, halogen or trifluoromethyl, W is halogen or ethenoxy and $W_1$ is hydrogen or halogen; (E) mono-higher alkyl quaternary ammonium salts selected from the group consisting of $C_8$ to $C_{22}$ alkyl isoquinolinium halides, $C_8$ to $C_{22}$ alkyl of pyridinium halides and salts having the formula

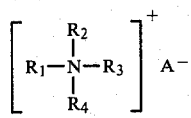

wherein $R_1$ is $C_8$ to $C_{22}$ alkyl, $R_2$ and $R_3$ are each $C_1$ to $C_3$ alkyl, $R_4$ is $C_1$ to $C_3$ alkyl or benzyl and A is selected from the group consisting of chlorine, bromine, iodine and methosulfate; (F) 5,7-diiodo-8 hydroxyquinoline; (G) 1,6-di(4'-chlorophenyldiguanado) hexane and (H) 5-chloro-2(2,4-dichlorophenoxy) phenol; and (II) a skin treating material selected from the group consisting of water-soluble polypeptides having a molecular weight of 120 to 20,000 which are derived by hydrolyzing a bone- or skin-derived collagen protein in the presence of acid, alkali or enzyme and polyethylene oxides having a molecular weight in the range of 500,000 to 400,000; and an aminopolyureylene resin having a molecular weight in the range of 300 to 100,000 and having the following repeating unit:

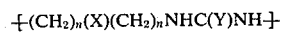

wherein X is $NH, N—C_1$ to $C_{22}$ alkyl,

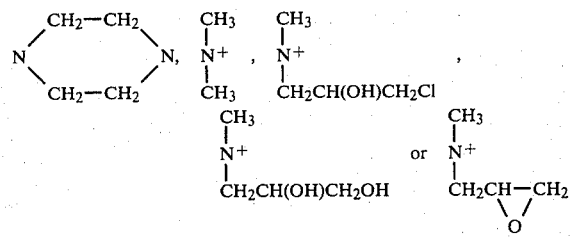

Y is O or S and n is 2 or 3, the weight ratio of resin to active material being from about 0.06 to 20:1 and being sufficient to improve the properties of said active material.

15. A method in accordance with claim 14 wherein said active material is said antimicrobial agent.

16. A method in accordance with claim 14 wherein said active material is said skin treating agent.

17. A method in accordance with claim 16 wherein said active material is said water-soluble polypeptide.

18. A method in accordance with claim 16 wherein said active material is said polyethylene oxide.

* * * * *